United States Patent [19]

Macoviak

[11] Patent Number: 5,738,649
[45] Date of Patent: Apr. 14, 1998

[54] PERIPHERAL ENTRY BIVENTRICULAR CATHETER SYSTEM FOR PROVIDING ACCESS TO THE HEART FOR CARDIOPULMONARY SURGERY OR FOR PROLONGED CIRCULATORY SUPPORT OF THE HEART

[75] Inventor: John A. Macoviak, Huntington Beach, Calif.

[73] Assignee: Cardeon Corporation, Saratoga, Calif.

[21] Appl. No.: 632,883

[22] Filed: Apr. 16, 1996

[51] Int. Cl.$^6$ .................................................. A61M 39/00
[52] U.S. Cl. ............................ 604/43; 604/53; 604/107; 604/282
[58] Field of Search .................... 604/40, 43, 53, 604/107, 264, 280, 282, 283, 284

[56] References Cited

U.S. PATENT DOCUMENTS

4,985,014  1/1991  Orejola ........................................ 604/43

Primary Examiner—Gary Jackson
Assistant Examiner—Julian W. Woo

[57] ABSTRACT

Described is a closed chest intravascular catheter system for a simultaneous biventricular approach to 1) intravascular cardiopulmonary surgery and 2) acute or prolonged mechanical circulatory support.

17 Claims, 5 Drawing Sheets

PERIPHERAL ENTRY BIVENTRICULAR CATHETER SYSTEM FOR PROVIDING ACCESS TO THE HEART FOR CARDIOPULMONARY SURGERY OR FOR PROLONGED CIRCULATORY SUPPORT OF THE HEART

This invention relates to a catheter system which facilitates cardiopulmonary surgeries and enables prolonged circulatory support of the heart.

BACKGROUND OF THE INVENTION

Heart surgery has generally required major open chest surgical procedures that put the patient to risk. Relatively high mortality rates and complications result from such invasive surgeries. Further, the surgeries require extensive hospitalization and recuperation time.

Surgical methods to correct heart problems are desirable which do not require open chest approaches. Some surgical techniques have been described for particular applications employing an intra-aortic catheter introduced into the vascular system of the patient. An example of such a technique may be found in U.S. Pat. No. 5,458,574. Endovascular techniques described to date, however, typically are not designed for all heart surgical procedures and do not provide access for robotic instruments to both sides of the heart.

Catheters have been described which access the left ventricle, for example, but there are none which are capable of surgically functioning on the right side of the heart. Further, such described catheters do not provide for a means to cross the atrial septum or provide for prolonged right or left ventricular bypass using an external pump, to mechanically support a reversibly failed heart in a closed chest procedure. Such a system which could be placed in both sides of the heart could more effectively resuscitate many cardiac arrest victims than other devices because ventricular decompression would be achievable.

Current methods further do not provide for selective cerebral perfusion, antegrade aortic flow, pulmonary artery flow or peripheral access vessel perfusion and drainage. Such mechanisms are necessary to minimize complications of a vast array related to proper direction of blood flow in the body.

Current methods do not take into account the desirability of perfusing the pulmonary artery or draining the left ventricle for prolonged support, (only those to acutely arrest the heart in open chest procedures) of the contracting but failed ventricle, via peripheral access for prolonged isolated right or left or simultaneous biventricular support. A system is needed which enables a broader range of endovascular cardiac surgical procedures, a method for prolonging heart support for certain surgical procedures and a method to mechanically support a reversibly failed heart to achieve direct circulatory arrest, with isolated cerebral perfusion using conventional heart and lung support machines.

SUMMARY OF THE INVENTION

The present invention provides a peripheral vascular catheter system versatile enough to robotically access both sides of the heart, provide for prolonged heart support (to mechanically support a reversibly failed heart) to achieve deep hypothermic circulatory arrest with isolated cerebral perfusion enabling surgery on the non-beating heart while protecting blood flow to the brain. The subject biventricular vascular catheter system comprises (a) an elongated catheter shaft advanceable from a peripheral vessel to and through all chambers of the heart, including across the ventricular or atrial septum, having a proximal end adapted to extend out of the patient and a distal end adapted to move through the chambers of the heart, said distal end having multiple fenestrations and a first inner lumen extending therein from a port in the distal end of the shaft to a location in the proximal end; and (b) a succession of expandable members positioned along the catheter shaft such that after the catheter has been positioned in the left heart of the patient's body, the first expandable member is located at the proximal end of the catheter shaft at the site of entry of the shaft into the patient, the second expandable member is located distal to the first expandable member which is dimensioned and configured so that it sits in the proximal descending thoracic aorta, a third expandable member distal to the second expandable member which is dimensioned and configured so that it seats between the coronary ostia and the brachiocephalic artery and a fourth expandable member distal to the third expandable member which is dimensioned and configured so that it seats in the left ventricular outflow tract, each such expandable member having an interior which is in fluid communication with an inflation lumen extending within the catheter shaft from a location from within the respective expandable member to a location in the proximal portion which is adapted to extend out of the patient. The same catheter may optionally be placed in the right heart.

Preferably the catheter system will also have a second limb branch catheter connected to the catheter shaft at the proximal end, said limb catheter disposed to provide for drainage or perfusion of the peripheral vessel used as an entry for the catheter shaft in order to protect the limb vasculature. Such limb catheters allow drainage or perfusion of the vessel entered to permit continual placement of the catheter for several days, if necessary, for subacute cardiac assist. If neck vessels are accessed, for example, metabolic monitoring access to that limb or to cerebral circulation would be permitted.

The catheter system also preferably has a self-sealing dual diaphragm chamber instrument entry port branching from the more distal-ending channel of the catheter which has inflow and outflow ports to remove the air from the chamber to prevent an air embolus from occurring and to allow for the safe introduction of large devices.

In one preferred embodiment of the catheter system, the catheter has a catheter guide with at least one fenestration which enables the guidance of the catheter into and through the chambers of the heart and which may be removed from the catheter while the catheter is located within the heart.

Another preferred embodiment which facilitates the movement of the catheter through the heart includes multiple rings which extend axially around the shaft along a portion of the shaft proximal from the distal end and distal to the expandable member closest to the distal end. The rings are further supported by struts which connect the rings to one another. The struts are arranged so that they are positioned at varying points around the circumference of the catheter tip to prevent kinking.

The catheter system will further preferably accommodate the selective perfusion or drainage of blood either separately or at the same time.

The system described here encompasses a number of benefits including the following:

(a) the ability to perform intravascular cardiac and pulmonary surgery through the less complicated peripheral access as compared to standard sternotomy or thoracotomy;

(b) the system lessens blood loss, infection risk, pain, hospital stays, expense and delays in return to full activity;

(c) there would be an expected decrease in the possibility of air emboli to the brain when performing surgery inside the heart and with the chest closed compared to current open heart techniques;

(d) better control of myocardial temperature is afforded compared to open chest approaches;

(e) the ability to isolate subcirculation regions by selectively inflating the compartmentalizing expandable members to isolate sub-circulations such as the coronary, cerebral, pulmonary, neck and limb sub-circulations;

(f) the ability to perform antegrade aortic perfusion which avoids malperfusion;

(g) the ability to perform pulmonary artery perfusion which bypasses the right ventricle; and (h) the ability to optimally support the acutely failed heart by decompressing ventricles peripherally for acute and subacute mechanical circulatory support which would thus lead to an expected decrease in likelihood of infection, bleeding and pain compared to open chest cannulation for total ventricular support.

The major goals of the catheter system disclosed here are to provide a catheter and multiple compartment expandable member system, placed by cutdown or percutaneous techniques, for peripheral vessel entry to accomplish intravascular cardiopulmonary biventricular or two-sided access to robotic surgery techniques of intra-cardiopulmonary structures, provided by a system of single and/or double (major) channel catheters; acute (for a period of minutes) deep hypothermic circulatory arrest with the option for selective cerebral perfusion to enable intra-cardiopulmonary surgery; subacute (over a period of days) cardiopulmonary mechanical support, with antegrade aortic and/or pulmonary artery perfusion, biventricular decompression and peripheral vessel protection, to allow recovery of reversible heart failure.

Definitions

"Acute circulatory arrest" refers to the event where the patient's body is cooled (usually to about 10° C.), the assisting blood pump is stopped, and the blood is drained from the body.

"Subacute mechanical support" refers to the event where the circulation is mechanically assisted for multiple days.

"Reversible heart failure" refers to an acutely injured heart which is expected to recover over time.

"Retrograde" and "antegrade" when used herein in relation to the patient's vasculature, relate to the direction of normal blood flow and to the direction opposite normal blood flow through a vessel respectively.

The terms "proximal" and "distal" when used herein in relation to instruments used in a cardiac procedure, refer to directions closer and farther away, respectively, from that end of the instrument which is held or manipulated by the operator performing the procedure.

Terms relating to anatomical parts have the meaning ascribed to them in the art and when they are coupled with an instrument part (e.g. supra-coronary inflation member) they indicate where in the body the instrument part is to be located.

Other terms used herein, unless otherwise defined herein, have the meanings commonly used by those of skill in the art of cardiac surgery.

DESCRIPTION OF THE PREFERRED EMBODIMENT

The catheter system described herein with all of its preferred features represents a versatile system having multiple uses. The catheter is characterized by a flexible catheter shaft placed by surgical cutdown or needle/introducer guidewire technique into the vessels of the lower or upper extremity or neck. Larger internal vessels may also be used.

The catheter may have at least one or two major lumen channels. The major channel is a lumen large enough to carry blood and/or robotic instruments used for surgery and for visualization or other investigatory instrumentation. Minor lumen are used for expandable or inflatable members. They may also be used where smaller lumen are desired such as for cardioplegia. Although the catheter shaft may be provided with a single inflatable lumen, it is preferred to provide separate inflatable lumen for each expandable member so that their inflation and deflation can be controlled separately. The diameter of the catheter will vary depending upon the task to be performed and the size of the individual, usually about 5 mm to about 35 mm in outside diameter.

The catheter is constructed of thin walled soft flexible heparin coated polyurethane, polyethylene, polyvinyl chloride, polyfluorotetraethylene or similar durable plastic materials. Thin wall construction providing a maximum inner diameter is preferred.

Single and/or double major channel catheters are provided depending upon the situation. A single major channel catheter may be required for use in patients with small vessels or to deploy larger devices for intracardiac surgery. This then requires a separate perfusion catheter in the same circulatory system at a different site (venous or arterial). The double major channel catheter provides access for most goals through a single large artery and/or vein.

In the single channel setting, on the venous side the catheter may access and perfuse the pulmonary artery, or—traverse the atrial or ventricular septum through natural or created defects to facilitate robotic surgery. A second single channel catheter would drain the right ventricle and/or atrium back to the blood pump. When the heart is emptied and a bloodless surgical field is created, the distal robotic catheter could be positioned in the pulmonary artery, or enter the right or left ventricle or atrium from the right side for performing intraarterial or intracardiac surgery often in conjunction with a left sided robotically active complimentary catheter of the invention.

The double channel catheter, which may accomplish the same functional goals, enters only one vein if the vessels are large enough, instead of two veins which would be required in the single channel setting.

The catheter, when placed in the jugular vein, with a limb catheter component extending cranially, in the acute surgical setting, allows segmental isolation and drainage of the brain, and the ability to determine venous oxygen saturation.

Selective inflation of the compartmentalizing expandable members in the right heart allows isolation of the atrium from the vena cava or ventricle and the ventricle from the main pulmonary artery. Selective access to the coronary sinus, the right atrium, ventricle or pulmonary artery is thus facilitated.

On the arterial side the long single or double channel catheter would drain and access the left ventricle and/or left atrium and/or pulmonary veins in a retrograde approach. In the single channel setting a separate arterial catheter may enter the opposite limb artery and be advanced into the ascending aorta for antegrade systemic perfusion.

With the distal robotically active port of the catheter in the left heart, selective inflation of the different compartment expandable members permits isolation of the ventricle (sub-aortic compartment expandable member) from the coronary circulation, i.e. for administration of cardioplegia (supra-aortic compartment expandable member) which is thus separated from the systemic circulation, which in the setting of deep hypothermic circulatory arrest may be isolated from the perfuse cerebral circulation, by a proximal descending aortic compartment expandable member.

When used for intracardiac surgery on valves, septal defects, intra-cardiac masses, or in the pulmonary circulation, the creation of complete deep hypothermic circulatory arrest (DHCA) may be required to create a bloodless field. In certain situations it will be possible to achieve a bloodless field without DHCA. This would be by continuing the circulation but isolating bloodflow adequately from the cardioplegia-arrested heart and actively aspirating collateral bloodflow from the ventricle.

Because there is a proximal expandable member which would be inflatable in the proximal descending thoracic aorta, and because the aortic perfusion with this system is antegrade beginning just distal to the coronary arteries, with inflation of a supra-coronary expandable member and a proximal aortic expandable member, a low flow of blood through the aortic perfusion lumen could selectively be used to perfuse the cerebral circulation, during deep hypothermic circulatory arrest.

Imaging systems may be used to view the heart through the catheter, deployable devices such as heart valves may be passed through the catheter, and robotic instruments, including a scalpel, may be passed into the heart through the distal steering lumen to perform surgery with angioscopic visualization. Jet fluid infusion through the angioscope may clear the bloody field and allows direct visualization. Selective inflation of the expandable member system prevents regurgitation of fluid between compartments.

The catheter in its preferred form can be broken down into three major sectional components: (1) the distal floppy reinforced tip component, (2) the proximal component, and (3) the connection component.

1. The distal end. The catheters described here preferably have a distal floppy tip constructed of soft and flexible (floppy), non-kinking, reinforcement ringed, fenestrated, non-thrombogenic, thin-walled, durable synthetic material. The distal tip has at least one fenestration to allow passage of robotic intracardiac surgerical devices.

The catheters may be introduced either antegrade or retrograde, through heart valves, by, preferably, a retractable, fenestrated removable tip guide with a guide wire that will be passed through the steering lumen. The distal component extends proximally to the most distal compartment expandable member. The construction of the distal tip component is to enable multiple 360 degree rotations and serpiginous conformations without kinking the catheter, thus avoiding obstruction to blood flow and allowing robotic steering for intra-cardiac or intra-pulmonary vascular surgery.

The distal component begins at the distal (subaortic or supra-pulmonic) compartment expandable member and has multiple sideholes in the floppy tip for drainage of blood from the left ventricle or atrium or perfusion of blood into the pulmonary artery. A central end hole permits exit of robotic surgical instruments and angioscope from the drainage/steering lumen.

The most distal compartment expandable member in the left heart prevents regurgitation of fluid or blood from the aorta into the left ventricle, and from the pulmonary artery into the right ventricle in the right heart. The removable guide will typically have a sliding central flexible wire guide to accurately direct the catheter centrally. The guide and tip may be removed once the catheter is in position.

2. The proximal component. The proximal component of the catheter will have compartment expandable members ranging in number from three or more. Perfusion ports will typically be distally located between the most distal and the more proximal compartment expandable members to perfuse the coronary, cerebral sub-circulations through minor lumens. Antegrade systemic circulatory flow is provided by a major single or double channel catheter opening in the ascending aorta.

The catheter will typically have separate minor small lumen port exits between the distal expandable member and the supra-coronary aortic expandable member for coronary artery perfusion.

The number of compartment expandable members and number of perfusion ports will relate to the size of the individual and the circulatory pattern selected. Infusion of cardioplegia into the coronary arteries will be by a separate coronary perfusion port lumen in the catheter which can be selectively infused.

In the certain embodiments of the double channel design, the two channels can slide independently from each other to optimize positioning of one relative to the other.

In the non-sliding double channel embodiments, an especially ultra-thin wall will exist between the inner and outer lumen, to maximize lumen diameters, yet be strong by virtue of its flat shape supported by the outer walls of the catheter.

In the left heart situation, the first more proximal supra-aortic valve expandable member is just proximal to the distal end of the proximal component which inflates into the aorta above the coronaries and below the innominate artery with distal side ports to allow infusion of cardioplegia. Between the most distal compartment expandable member and the first more proximal expandable member, are the side ports for coronary artery access.

The cerebral circulation can be perfused antegrade from the major channel opening into the ascending aorta, during circulatory arrest with inflation of the more distal and supra aortic (one above the coronary arteries) the proximal descending thoracic aorta compartment expandable members.

In the right heart, perfusion of the pulmonary artery is performed through the distal component lumen, and the right heart is drained by the more proximally located major channel of a double or single major channel catheter. This is the optimal arrangement to support isolated right ventricular failure.

A more proximal compartment expandable member positioned into the inflow of the right atrium allows isolated coronary sinus perfusion, through a minor perfusion lumen, when that expandable member and a compartment expandable member beyond the coronary sinus are inflated.

3. The connection component. The connection component has the most proximal compartment expandable member to prevent leakage from the vessel through which entry is gained.

The connection component will typically have a side perfusion limb from the major perfusion channel which is placed into the distal entered peripheral artery with its seating compartment expandable member. When the venous circulation is catheterized, a limb/jugular drainage catheter with compartment seating expandable member is placed in the distal vessel and drains venous blood into the major venous channel of the catheter.

An access diaphragm sealer built into the connection component is used to place the robotic instruments without air or fluid entry or leakage. The dual diaphragm chambered vascular access port (DDCVAP) is constructed of flexible synthetic material with spiral cross and counter cross reinforcement supports in the intravascular component. It may be constructed so that it is inserted within the entry vessel or so that it is a separate component residing outside of the body. A removable semirigid pointed inner guide with guide wire lumen, can be used for percutaneous or open vascular placement. The DDCVAP preferably has four features: (1) an outer soft diaphragm with self-sealing penetratable center opening, (2) an inner soft diaphragm of similar construction, (3) an aspiration port from the chamber between the diaphragms, and (4) a fluid infusion port into the chamber.

The chamber acts as an air lock and washout lock which is necessary when introducing large devices into the vascular system to prevent air embolization and fluid leakage. It minimizes trauma to repeated entries of large devices. The DDCVAP can be directly inserted into a vessel to allow passage of robotic instruments or intravascular devices.

The DDCVAP is designed also as the access port component of the outside connection component of a system as described here.

The ports for the minor lumens for perfusion of a compartment between expandable members or to fluid inflate the compartment expandable members, are located outside the vessel entered as part of the connection component.

The major attributes of the system with its preferred embodiments are its ultra-thin walled, flexible reinforced non-kinking double and/or single major channel catheters with inflatable/deflatable expandable members which compartmentalize the circulatory system into sub-circulatory systems to specifically include coronary, cerebral and limb or neck peripheral access vessels. Minor lumen are used for expandable member inflation/deflation control.

Entry site limb catheters allow drainage or perfusion of the vessel entered to permit continual placement of the catheter for several days, if necessary for subacute cardiac assist, to protect the limb vasculature entered. This also permits metabolic monitoring access to that limb or cerebral circulation, in the case of neck vessels accessed.

Implementation

The system also achieves complete decompression (by direct drainage) of either or both ventricles. Further, active or passive return of the intra-cardiac blood to a blood pump of unoxygenated blood (directly from the right ventricle) or oxygen enriched blood (directly from the left ventricle) is achieved along with antegrade perfusion of the pulmonary artery or aorta. The blood at the system level of the pump may or may not require oxygen enrichment. The described compartment expandable members prevent catheter migration and regurgitant blood/fluid flow between compartments. This may be used to improve the creation of a bloodless surgical field in the heart chamber to be operated. It also permits selective perfusion or drainage of a selected sub-circulatory system, i.e. the brain, heart or limb.

A catheter system is contemplated herein that includes multiple catheters as described which differ from each other in their outside diameters. The catheter system may further contain multiple catheters that have expandable members in varying positions from which a selection can be made depending upon the task to be performed and the patient's needs.

Figure 1:
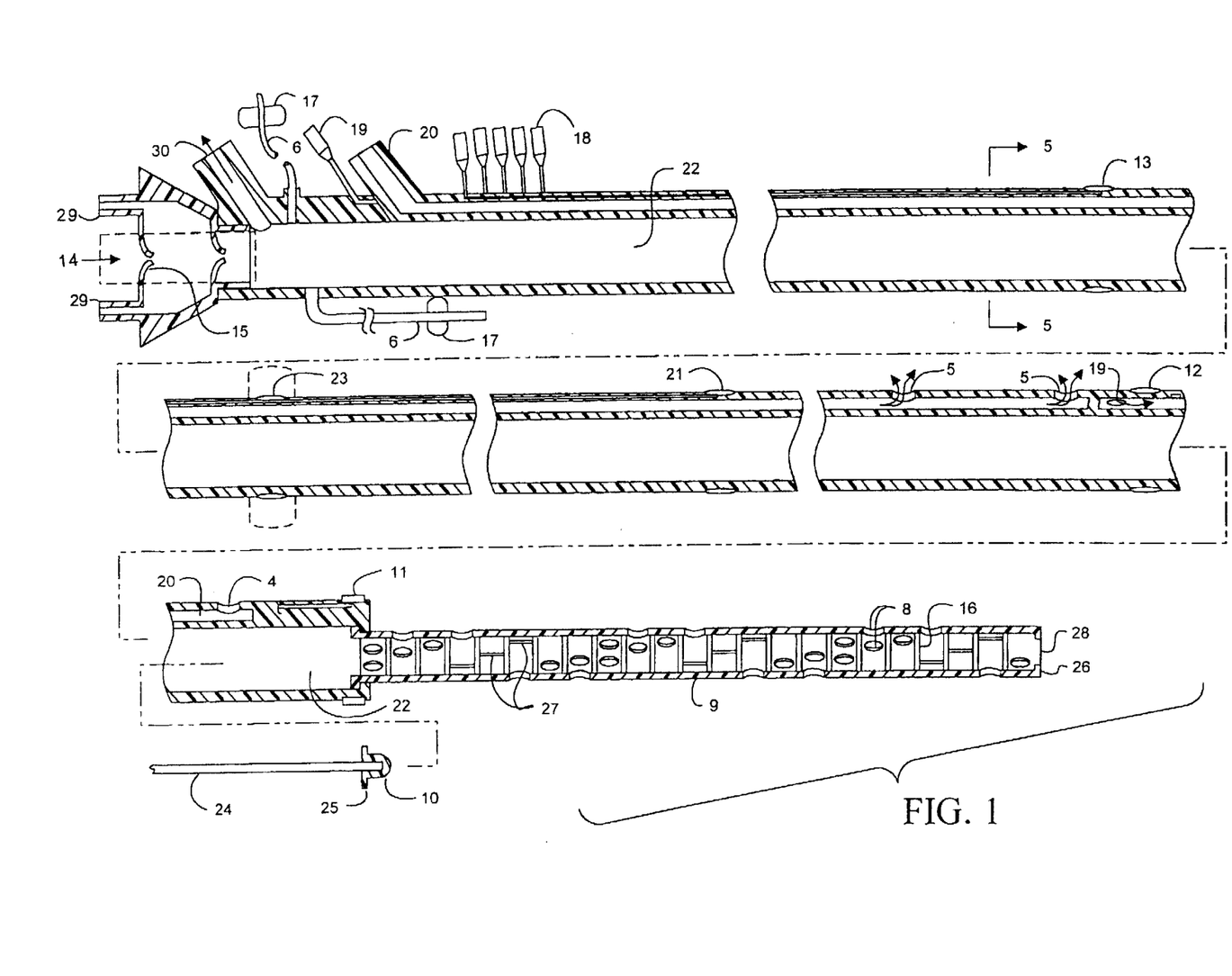
FIG. 1 schematically illustrates a cardiac access catheter system embodying features of the invention.

The catheter system can be further explained with reference to the accompanying figures:

FIG. 1 depicts elements of a catheter system as described herein. At the distal end of the catheter is a removable and retractable catheter guide (10) which has at least one fenestration (8) to permit fluids to pass through the catheter as it moves through the body. The guide may be retracted from the catheter when desired by simply pulling out the guide by the retractor rod (24). Typically this is done when the catheter is in place within the heart. A bullet shape for the guide is preferred and allows for less traumatic penetration across the heart valves or narrowings. A lip (25) is provided on the guide to match a ledge (26) at the end of the catheter tip. The ledge (26) catches the lip (25) so that the guide will pull the catheter system through the body. The floppy tip (9) through which the catheter guide slides extends from the open end steering robotic channel (22) to the distal compartment expandable member (11).

Figure 2:
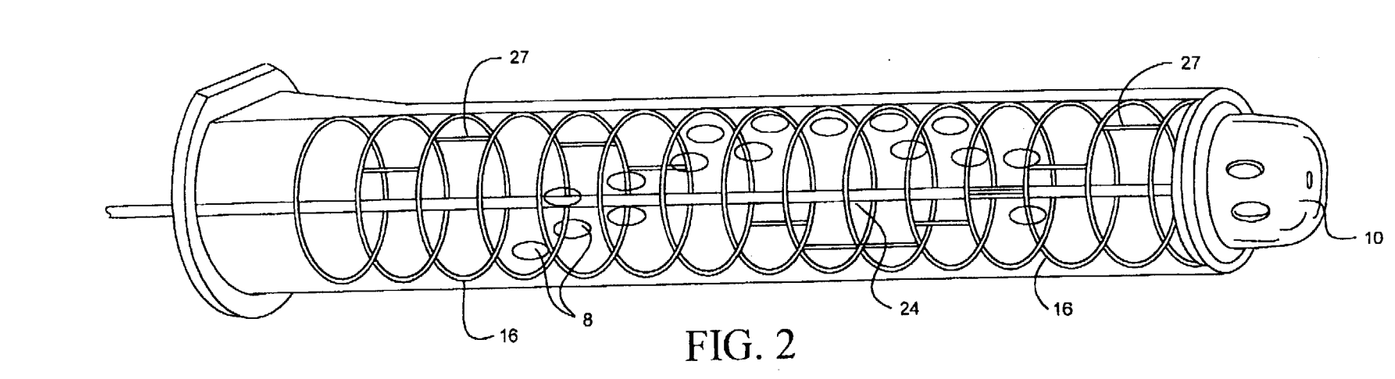
FIG. 2 illustrates the preferred fenestrated floppy tip and fenestrated removable catheter guide.

The floppy tip preferably has multiple ring members (16) which support the catheter shaft and multiple fenestrations (8) placed between various ring members which allow fluid flow through the catheter. The ring members are held together and further supported by a support strut (27) bridging two consecutive rings. It is preferred that the support struts be placed perpendicular to the rings and be arranged randomly or distant from each other around the circumference of the tip. The floppy tip and the removable catheter guide are illustrated in more detail in FIG. 2.

At the proximal end of the floppy tip (9) is the open end steering robotic channel (22). There is a distal expandable member (11) near the distal end of the lumen and just proximal to the floppy tip. The expandable members will typically surround the catheter shaft circumferentially, particularly when expanded. Proximal to the distal expandable member is a perfusion port (4) which typically will be in fluid connection with the coronary artery or sinus limb through a channel (20). Aortic perfusion ports (5) are located just proximal to the aortic expandable member (12). A channel (20) for these ports provides fluid connection along the course of the catheter. For example, the blood channel (20) provides a means to carry blood to and from the aorta. Minor lumen can be used to infuse cardioplegia, as desired. These ports (5) provide a path through which blood may be returned to the patient in the aorta, or drained from the right heart in the opposite direction. One optional embodiment of the catheter described herein omits the presence of the proximal component channel (20).

Other expandable members (12), (23), (13) and (17) are positioned along the catheter and proximal to the distal expandable member (11). Each such expandable member has an interior which is in fluid communication with an inflation lumen extending within the catheter shaft from a location within the respective expandable member to a balloon port (18) in the proximal portion which is adapted to extend out of the patient. It is preferred that expandable members be positioned along the catheter shaft such that after the catheter has been positioned in the patient's body, a first expandable member is located at the proximal end of the catheter shaft at the site of entry of the shaft into the patient, a second expandable member is located distal to the first expandable member which is dimensioned and configured so that it may sit in the proximal descending thoracic aorta, a third expandable member distal to the second expandable member is dimensioned and configured so that it may sit between the coronary ostia and the brachiocephalic artery and a fourth expandable member distal to the third expandable member is dimensioned and configured so that it may sit in the left ventricular outflow tract. A proximal descending thoracic aortic expandable member such as one analogous to that of the expandable member (12) allows compartmentalization of the cerebral circulation between that and a coronary expandable member such as one analogous to that of the expandable member (4). Perfusion from the aortic perfusion channel (20) allows selective cerebral perfusion during deep hypothermic circulatory arrest. Expandable member ports (18) may be provided which allow further selective inflation or deflation of compartment expandable members.

Limb drainage (venous) (6) or perfusion (arterial) (6) with compartment expandable members (17), may be used for longer surgical procedures.

The diaphragmed entry port (14) is at the most proximal end of the catheter, has a self-sealing dual diaphragm (15) and provides for catheter steering and entry of robotic instruments. The entry port (14) has entrance and exit ports (29) through which fluid can be permitted to flow through the entry port primarily to flush air out of the port after the robotic instruments are placed into the entry port. Typically a lumen branch (30) will be provided to permit flow of fluids from the catheter to be diverted away from the entry port.

Figure 3:
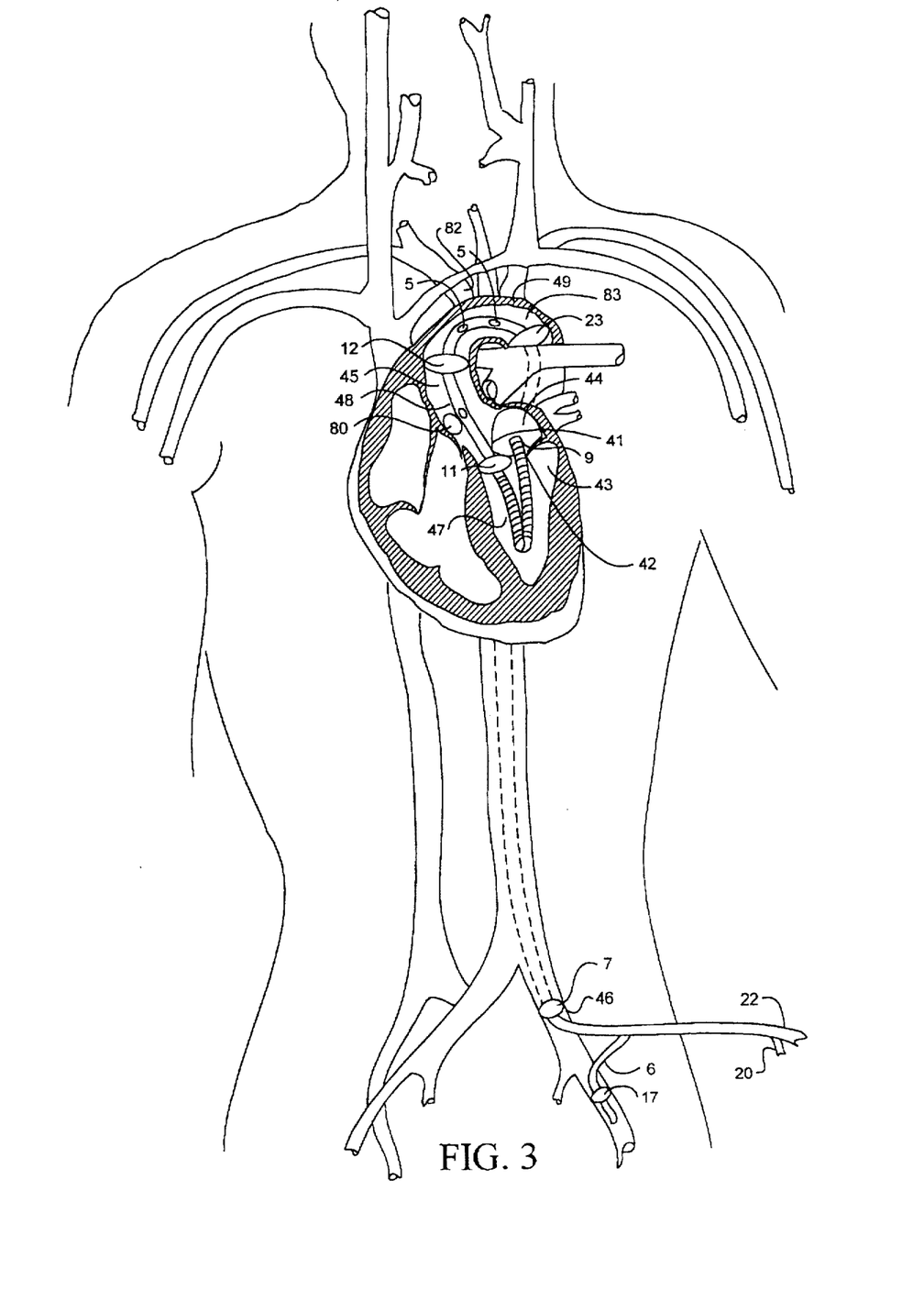
FIG. 3 illustrates a system as placed into the left heart by entering a single iliac artery.

FIG. 3 illustrates a system as placed into the left heart by entering a single iliac artery. The fenestrated floppy tip (9) is illustrated traversing the aortic (41) and mitral valve (42) to place the open robotic channel (22) in the left heart chambers (44, left atrium and 43, left ventricle). The distal seating expandable member (11) sits in the left ventricular outflow tract (47) to prevent fluid from above the aortic valve (41) from entering the left ventricle (43). The coronary sinus lumen (48) between the distal (11) and the ascending aortic expandable member (12) is positioned between the coronary ostia (80) and the brachiocephalic artery (82) to infuse the two coronary ostia (80) by flooding the ascending aorta (40), between the expandable members or just above the aortic valve. An expandable member (23) sits in the proximal descending thoracic aorta (83).

The aortic perfusion ports (5) sit in the ascending aorta (45) and aortic arch (49) to provide antegrade blood flow in the majority of the aorta. The entry site is into the iliac artery (46) with the connecting components outside the artery. The seating expandable member (7) on the main catheter inside the iliac artery (46) and (17) on the distal limb perfusion catheter (6) is also shown.

If one catheter is used to enter each iliac artery to access the left heart, one catheter traverses the iliac artery to the left heart chamber. This enables placement of a larger single channel catheter for robotic procedures in the opposite iliac artery, but necessitates a contralateral arterial perfusion catheter.

Figure 4:
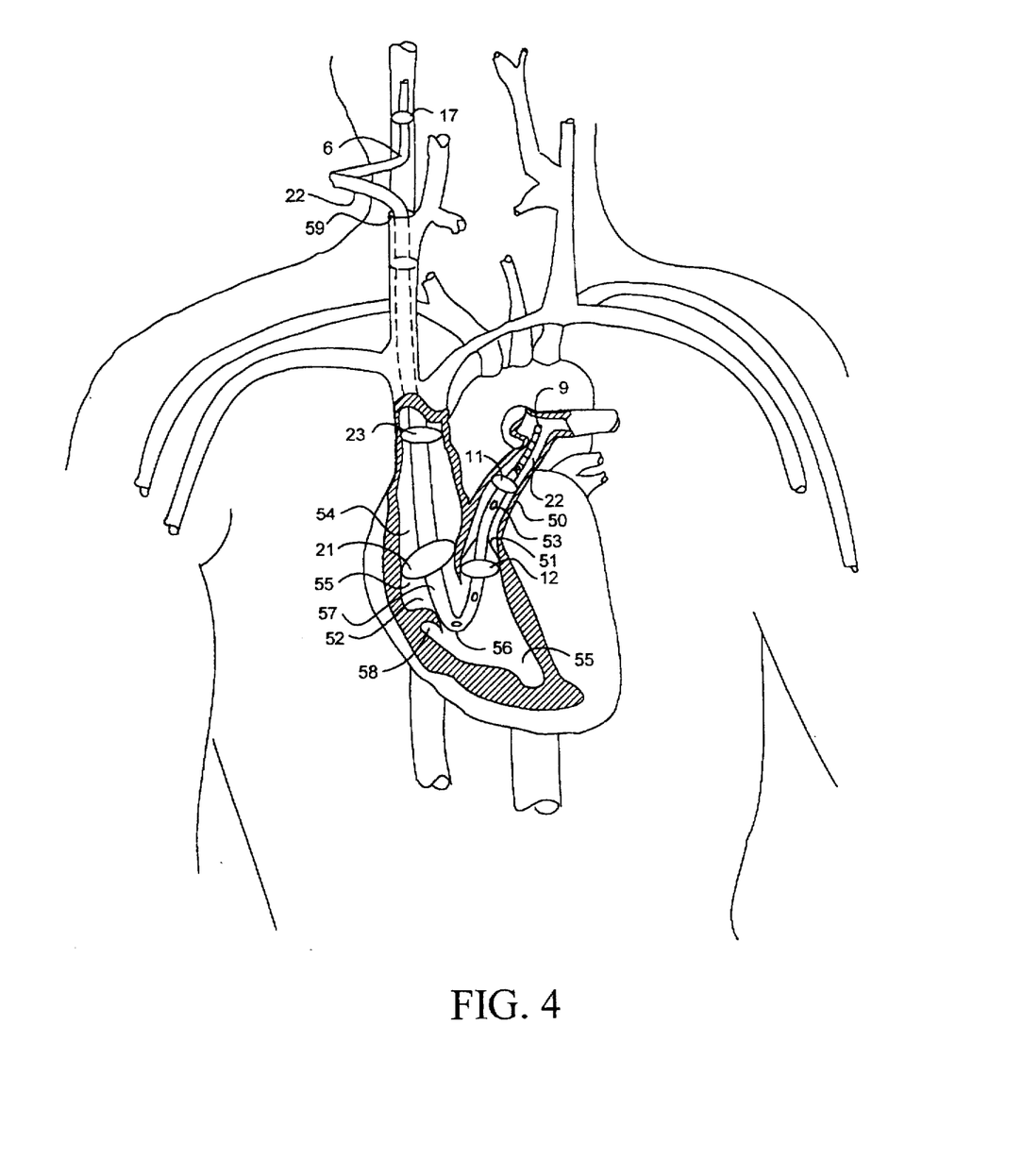
FIG. 4 illustrates a system as placed in the right heart by entering the jugular vein.

FIG. 4 illustrates a system in the right heart entering a single vein. The distal floppy tip component (9) of the catheter is placed in the main pulmonary artery (50) after having traversed the tricuspid (52) and pulmonic valves (51). In this position the major distal channel (22) may perfuse the pulmonary artery (50) or provide robotic access to the right heart (54, right atrium and 55, right ventricle). The distal seating expandable member (11) prevents regurgitation of blood into the right heart. The proximal drainage ports (56), which are positioned in the right ventricle (55), communicate with the outer proximal channel (20, FIG. 1) to drain blood from the right heart to the outside. A seating expandable member (23), at the opening of the right atrium (54) prevents regurgitation of fluid from the right atrium (54). The coronary sinus perfusion port (57) is shown near the coronary sinus (58). An expandable member (12) seats the catheter in position just below the pulmonic valve (53) and another expandable member (21) seats the catheter in position at the coronary sinus. The major channel (22) enters the jugular vein (59) with a limb catheter (6) seated by an expandable member (17) drains the occluded vein proximally.

If two separate veins are used to enter the right heart, a single channel catheter may be used to enter the jugular vein to access the pulmonary artery and right heart with the floppy tip. The single channel will allow a larger catheter for robotic surgery. Another single channel catheter could be used to enter the iliac vein to enter the right heart for drainage. Preferably a limb catheter with a seating expandable member would be used to drain the distal limb.

Figure 5:
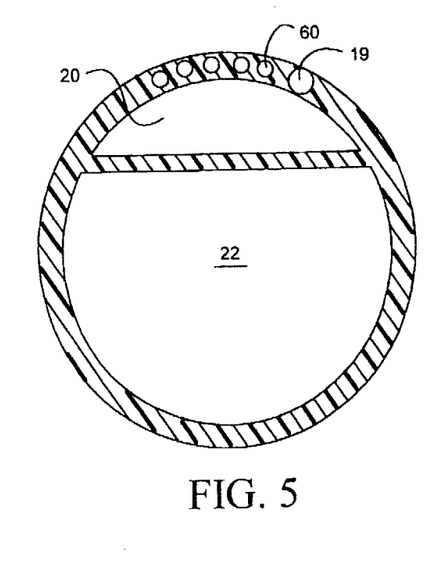
FIG. 5 illustrates a cross-section view of the catheter depicted in FIG. 1, where indicated in FIG. 1.

FIG. 5 shows a cross-section of the double major channel and multiple minor lumen construction taken at the point indicated in FIG. 1. The major channel (22) allows for placement of robotic instruments and has an outer thin wall which separates it from another major, but smaller channel (20). Minor lumen (19) and channel (20) permit the inflow and outflow of fluids as required for the particular surgery and minor lumens (60) permit the fluid connection for inflation of the expandable members. The minor lumens are used as non-robotic perfusion lumens.

Figure 6:
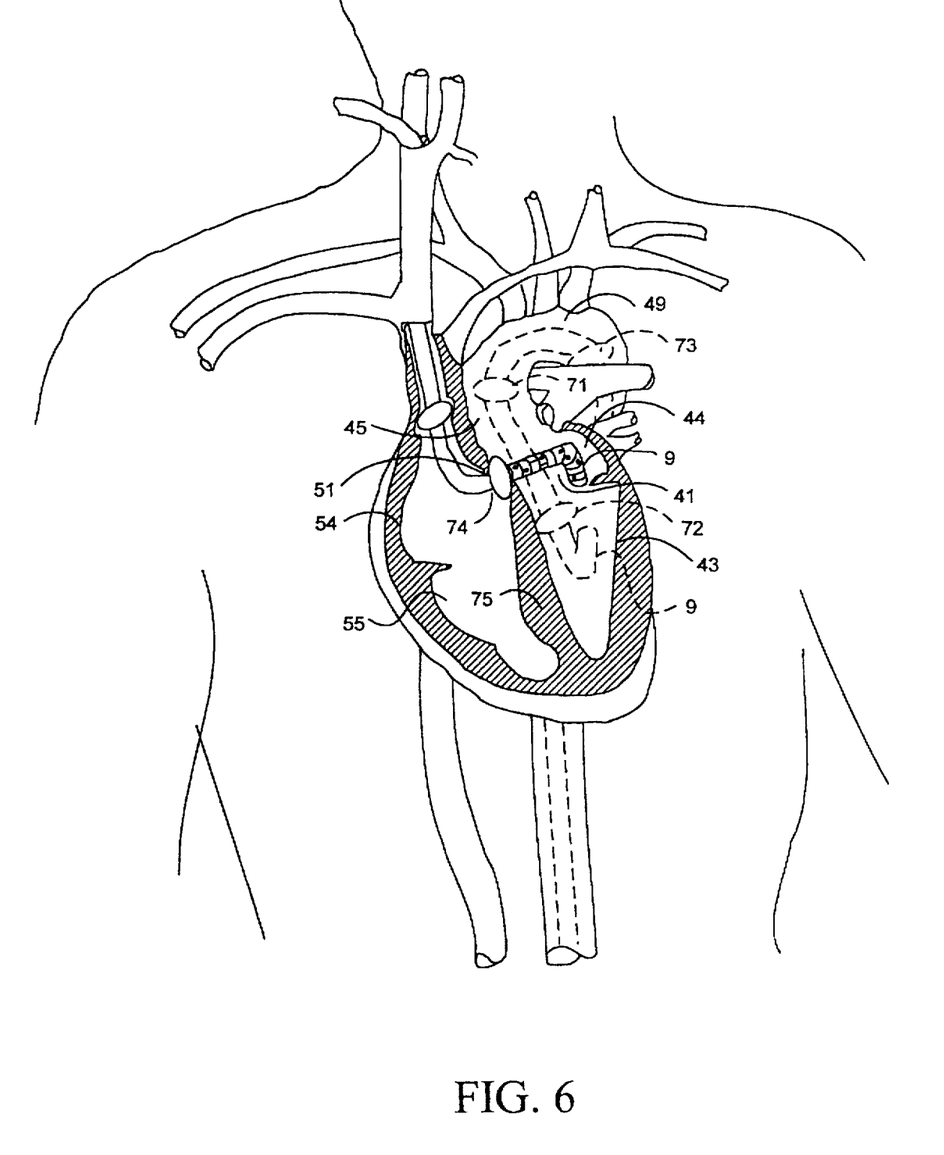
FIG. 6 illustrates a catheter system showing transeptal complimentary catheters.

FIG. 6 illustrates a system showing transeptal complimentary catheters. An exemplary method of performing biventricular robotic transeptal surgery on intracardiac structures and achieving deep hypothermic circulatory arrest is as follows:

A. The distal end component (9) of the catheter system is advanced to a location inside the left heart by peripheral vascular entry, which by way of specifically designed catheters traverses the aortic valve (41) with a retractable guide, and provides access for specifically designed "robotic" instruments and angioscopic or other imaging catheters to enter the inner chambers of the left heart through the aortic valve (41).

B. A major channel is used to empty the left ventricle (43) into a blood reservoir through its blood channel, then to be pumped back through the more proximally terminating blood channel into the aortic arch (49) while the blood is oxygen enriched and cooled to achieve hypothermic circulatory arrest. One expandable member is inflated to seat the catheter in the entry vessel and the distal expandable member (71) is inflated to prevent regurgitant flow from the aorta into the left heart.

C. Simultaneously, a catheter is advanced through a peripheral vein into the right heart with the distal component end placed in the right atrium and advanced across the septum into the left atrium (44). The more proximal blood channel ends in the right atrium. Blood is drained from both channels into the blood reservoir to be cooled, oxygen-enriched and pumped back to the patient through the proximal ascending aortic blood channel.

D. Once the patient is sufficiently cooled a proximal descending thoracic aortic expandable member (72) is inflated and a proximal ascending aortic expandable member (71) are inflated to allow low flow selective perfusion of the aortic arch vessels while the body is otherwise emptied of blood to create a bloodless surgical field.

E. With circulatory arrest the proximal channel of the venous drains blood from the right heart returning from perfusing the brain. The distal tip component (9) from the right heart can be positioned across the atrial septum (74) or into the left ventricle (55) for dual left heart access in synchrony with the left ventricular catheter advanced from the aorta end component. Access may be had to all intracardiac structures from either side of the structure including all four heart valves and both atrial and ventricular septal defects simultaneously from the right and left heart vantages thus enabling complimentary actions on either side of the surgical target. If a septal defect is not congenitally present and transeptal access is needed, a robotic scalpel is used to create such a defect.

F. Upon completion of surgery, the proximal ascending and proximal descending thoracic aortic expandable members are deflated and full blood flow is reestablished as at the outset of the procedure until the patient is fully rewarmed and cardiopulmonary bypass is weaned off.

G. Should a patient require prolonged mechanical support the catheters are advanced as described above with the right heart catheter having its tip in the pulmonary artery. If isolated right heart bypass is elected the blood is drained from the proximal intracardiac blood channel and oxygenated (optional) blood is pumped back into the pulmonary artery through the distal channel. If complete biventricular bypass is required both the blood channels of the right heart catheter drain blood back to the heart pump, oxygenated there and pumped back into the ascending aortic component.

H. For left heart support the distal end component of the left heart is advanced into the left ventricle and blood is drained from that channel back to the blood pump reservoir and oxygen enriched (optional) and pumped back through the proximal ascending aortic channel with or without the blood drained from the right heart.

The above method allows atraumatic prolonged presence of the distal end component in the heart while the right or left or both heart(s) is (are) beating and being mechanically supported.

What is claimed is:

1. A biventricular vascular catheter system for providing access to a patient's heart for cardiopulmonary surgery or for prolonged cardiopulmonary circulatory support of the heart comprising:
(a) an elongated catheter shaft advanceable from a peripheral vessel to and through all chambers of the heart, including across a septum, having a proximal end adapted to extend out of the patient and a distal end adapted to move through the chambers of the heart, said distal end having multiple fenestrations and a first inner lumen extending therein from a port in the distal end of the shaft to a location in the proximal end; and
(b) a succession of expandable members positioned along the catheter shaft such that after the catheter has been positioned in the patient's body in a left heart, the first expandable member is located at the proximal end of the catheter shaft at the site of entry of the shaft into the patient, the second expandable member is located distal to the first expandable member which is dimensioned and configured so that it seats in the proximal descending thoracic aorta, a third expandable member distal to the second expandable member which is dimensioned and configured so that it seats between the coronary ostia and the brachiocephalic artery and a fourth expandable member distal to the third expandable member which is dimensioned and configured so that it seats in the left ventricular outflow tract, each such expandable member having an interior which is in fluid communication with an inflation lumen extending within the catheter shaft from a location from within the respective expandable member to a location in the proximal portion which is adapted to extend out of the patient.

2. The catheter system of claim 1, further having a second limb branch catheter connected to the catheter shaft at the proximal end, said limb catheter disposed to provide for drainage or perfusion of the peripheral vessel used as an entry for the catheter shaft.

3. The catheter system of claim 1, further having a self-sealing dual diaphragm chamber instrument entry port branching from the more distal-ending channel of the catheter and having inflow and outflow ports to connect the major blood channels to an oxygenator pump.

4. The catheter system of claim 1, further having a bullet-shaped guide having fenestrations which enables the guidance of the catheter into and through the chambers of the heart and which may be removed from the catheter while the catheter is located within the heart.

5. The catheter system of claim 1, wherein the catheter shaft contains multiple rings which support the catheter shaft and which are located along a portion of the shaft proximal from the distal end and distal to the expandable member closest to the distal end.

6. The catheter system of claim 1, wherein the catheter accommodates the selective perfusion or drainage of blood either separately or at the same time.

7. The catheter system of claim 1, wherein the catheter contains at least five expandable members whose positions along the catheter shaft may be adjusted to expand at desired positions to compartmentalize subcirculations.

8. The catheter system of claim 1, wherein the system includes a scalpel, an imaging system, a deployable device and a robotic instrument which passes through a lumen of the catheter shaft and which incises the septum of the heart to permit passage of the catheter from one heart chamber to the other.

9. A catheter system which comprises multiple catheters of claim 1, wherein each of said multiple catheters differ from one another in their outside diameter.

10. A catheter system which comprises multiple catheters of claim 1, wherein each of said multiple catheters differ from one another in the positions of their expandable members.

11. A catheter system which comprises a catheter of claim 1, wherein said catheter has two channels which slide independently from each other.

12. An elongated catheter tip advanceable from a peripheral vessel to and through all chambers of the heart, including across a septum, having a flexible shaft with a removable guide tip which slides within the shaft and a succession of rings which support the shaft wherein the rings are further supported by struts bridging two successive rings, said struts further being variously positioned around the circumference of the catheter and further wherein the flexible shaft contains one or more fenestrations.

13. A method for surgery of the left heart comprising:
 (a) advancing to a location within a patient's left heart chamber an elongated catheter advanceable from a peripheral vessel, said catheter having:
  (i) a proximal end that is adapted to extend out of the patient;
  (ii) a distal end that comprises a flexible retractable (removable) tip with multiple fenestrations and a succession of rings placed proximal from the distal end which support a lumen and which are further supported by struts bridging two successive rings, said struts further being variously positioned around the circumference of the catheter;
  (iii) a succession of expandable members positioned along the catheter shaft such that after the catheter has been positioned in the patient's body, the first expandable member is located at the proximal end of the catheter shaft at the site of entry of the shaft into the patient, the second expandable member is located distal to the first expandable member which is dimensioned and configured so that it seats in a proximal descending thoracic aorta, a third expandable member distal to the second expandable member which is dimensioned and configured so that it seats between coronary ostia and a brachiocephalic artery and a fourth expandable member distal to the third expandable member which is dimensioned and configured so that it sits in the left ventricular outflow tract, each such expandable member having an interior which is in fluid communication with an inflation lumen extending within the catheter shaft from a location from within the respective expandable member to a location in the proximal portion which is adapted to extend out of the patient; and
 (b) inserting robotic instruments for surgery into the catheter.

14. The method of claim 13, further wherein a limb catheter is attached to the catheter of claim 13 to perfuse an artery.

15. A method for surgery of the right heart comprising:
 (a) advancing to a location within a patient's right heart chamber an elongated catheter advanceable from a peripheral vessel, said catheter having:
  (i) a proximal end that is adapted to extend out of the patient;
  (ii) a distal end that comprises a flexible retractable (removable) tip with multiple fenestrations and a succession of rings placed proximal from the distal end which support a lumen and which are further supported by struts bridging two successive rings, said struts further being variously positioned around the circumference of the catheter;
  (iii) a succession of expandable members positioned along the catheter shaft such that after the catheter has been positioned in the patient's body, the first expandable member is located at the proximal end of the catheter shaft at the site of entry of the shaft into the patient, the second expandable member is located distal to the first expandable member which is dimensioned and configured so that it seats at the opening of a right atrium, a third expandable member distal to the second expandable member which is dimensioned and configured so that it seats the catheter at a coronary sinus and a fourth expandable member distal to the third expandable member which is dimensioned and configured so that it sits distal along the catheter to a pulmonic valve, each such expandable member having an interior which is in fluid communication with an inflation lumen extending within the catheter shaft from a location from within the respective expandable member to a location in the proximal portion which is adapted to extend out of the patient; and
 (b) inserting robotic instruments for surgery into the catheter, and adjusting or steering the distal end to access a right heart structure and a pulmonary artery.

16. The method of claim 15, further wherein a limb catheter is attached to the catheter of claim 15 to drain a vein.

17. A method for trans-septal surgery of a heart comprising:
 (a) advancing to a location within a patient's left heart chamber an elongated catheter advanceable from a peripheral vessel, said catheter having:
  (i) a proximal end that is adapted to extend out of the patient;
  (ii) a distal end that comprises a flexible retractable (removable) tip with multiple fenestrations and a succession of rings placed proximal from the distal end which support a lumen and which are further supported by struts bridging two successive rings, said struts further being variously positioned around the circumference of the catheter;
 (b) advancing a catheter as described in step (a) above into a location into the right heart; and further advancing the catheter across;
 (c) advancing either the catheter of step (a) or the catheter of step (b) across an atrial or a ventricular septum; and
 (d) inserting robotic instruments for surgery into either the catheter of step (a) or step (b).

* * * * *